(12) United States Patent
Krill et al.

(10) Patent No.: US 6,441,199 B2
(45) Date of Patent: Aug. 27, 2002

(54) PROCESS FOR THE PRODUCTION OF α-TOCOPHEROL ACETATE BY CONDENSATION OF TRIMETHYLHYDROQUINONE WITH ISOPHYTOL WITH RECYCLING OF AN ACETIC CATALYST SOLUTION

(75) Inventors: Steffen Krill, Speyer; Stepahn Kretz, Biebergemünd; Klaus Huthmacher, Gelnhausen, all of (DE)

(73) Assignee: Degussa AG, Frankfurt am Main (DE)

( * ) Notice: Subject to any disclaimer, the term of this patent is extended or adjusted under 35 U.S.C. 154(b) by 0 days.

(21) Appl. No.: 09/801,091

(22) Filed: Mar. 8, 2001

(51) Int. Cl.⁷ ............................................. C07D 311/76
(52) U.S. Cl. ...................................... 549/408; 544/411
(58) Field of Search ................................. 549/411, 408

(56) References Cited

U.S. PATENT DOCUMENTS 5,468,883 A * 11/1995 Grafen et al. ............... 549/411
6,005,122 A * 12/1999 Baldenius et al. ........... 549/410
6,239,294 B1 * 5/2001 Krill et al. .................. 549/408

FOREIGN PATENT DOCUMENTS

| EP | 0087576 | * | 7/1982 | ................. 549/411 |
| EP | 0 850 937 |  | 7/1998 |  |
| JP | 51080859 | * | 7/1976 | ................. 549/411 |

OTHER PUBLICATIONS

Chemical Abstracts, vol. 86, No. 13, 1977.
English language abstract of reference LR above.

* cited by examiner

*Primary Examiner*—Alan L. Rotman
*Assistant Examiner*—Raymond Covington
(74) *Attorney, Agent, or Firm*—Pillsbury Winthrop LLP

(57) ABSTRACT

A process for the production of α-tocopherol acetate in a recirculating process by condensation of trimethylhydroquinone and isophytol in the presence of a catalyst system of a zinc halide and an aqueous protonic acid and, optionally, an elemental metal, in a polar solvent/water mixture extractable or miscible with water, and subsequent acylation of the resultant α-tocopherol and recirculation of the catalyst system.

9 Claims, 1 Drawing Sheet

PROCESS FOR THE PRODUCTION OF α-TOCOPHEROL ACETATE BY CONDENSATION OF TRIMETHYLHYDROQUINONE WITH ISOPHYTOL WITH RECYCLING OF AN ACETIC CATALYST SOLUTION

CROSS-REFERENCE TO RELATED APPLICATION

This application is based on German Application DE 100 11 403.2, filed Mar. 9, 2000, which disclosure is incorporated herein by reference.

FIELD OF THE INVENTION

This invention relates to an improved process for the production of alpha-tocopherol acetate by condensation of trimethylhydroquinone and isophytol in the presence of a catalyst system of a zinc halide and an aqueous Brønsted acid and optionally an elemental metal as a third component, wherein the reaction is performed in a polar, protic solvent extractable or miscible with water, preferably acetic acid. After the condensation to yield alpha-tocopherol (α-tocopherol), a phase separation is performed to separate an acetic, aqueous catalyst phase and the resultant product solution separated from water is then esterified at moderate temperatures with an acylating agent, in the presence of the remaining catalyst components, Lewis acid/protonic acid, present in the product phase, and the solution of the catalysts obtained after working up by aqueous extraction after condensation, and acylation is regenerated by suitable methods and returned to the reaction as an acetic catalyst solution.

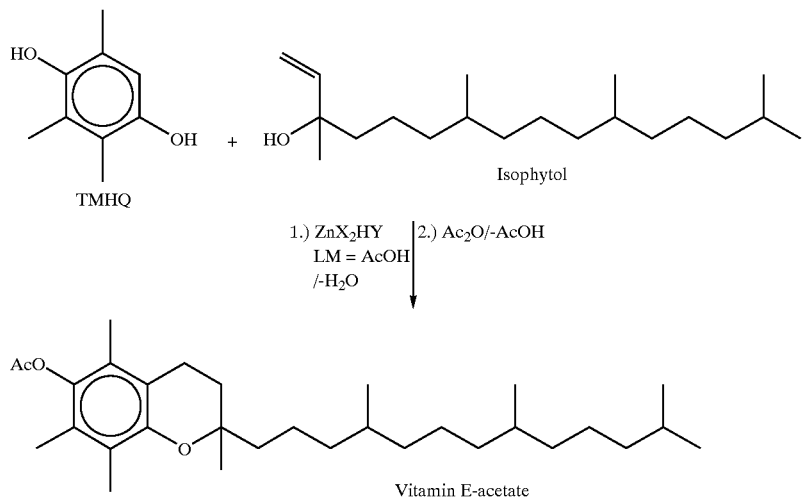

TMHQ=trimethylhydroquinone
$Ac_2O$=acetic anhydride
AcOH=acetic acid
LM=solvent
X=halide, hydroxide, oxide
Y=anion of a Brønsted acid.

α-Tocopherol and the derivatives thereof are of significance as feed additives, antioxidants, circulatory stimulants, agents for reducing cell aging and for associated applications. Pulverulent formulations of α-tocopherol acetate (vitamin E acetate) with a suitable silica are commercially known for feed additive applications.

BACKGROUND OF THE INVENTION

The processes which have primarily been described in the prior art are for the production of α-DL-tocopherol, i.e. the unesterified, non-storage-stable, photosensitive form of vitamin E. According to these processes, α-tocopherol is initially produced by condensation of trimethylhydroquinone with isophytol with condensation of water, and is esterified in a separate step with stoichiometric quantities of an acylating agent to yield vitamin E acetate. This method is illustrated in the following reaction scheme:

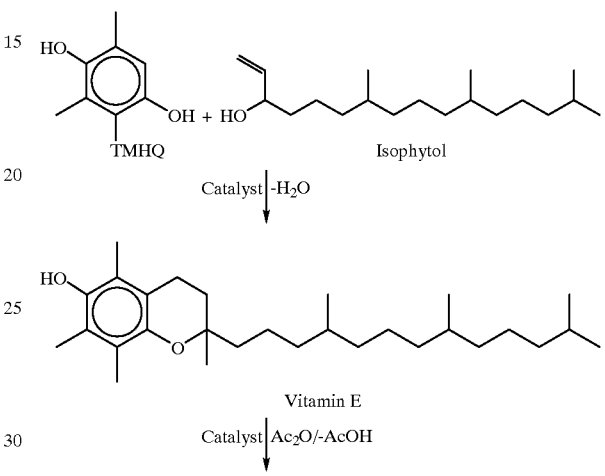

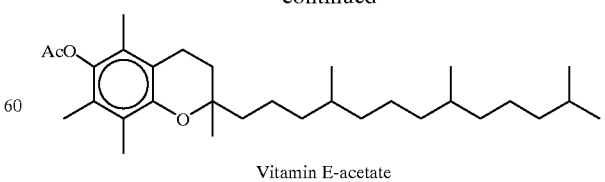

According to this prior art, the starting material is generally trimethylhydroquinone (TMHQ), which is reacted with isophytol using various catalyst systems. (U.S. Pat. No.

2,411,969, Hoffmann LaRoche; DE 3 203 487, BASF; U.S. Pat. No. 3,708,505, Diamond Shamrock, U.S. Pat. No. 4,239,691, Eastman Kodak; as well as DE-OS 42 43 464. U.S. Pat. No. 5,523,420, DE-OS 4243464, EP 0 694 541, and DE 196 03 142). The catalysts used for the reaction are generally combinations of Lewis acids, in particular zinc halides, and protonic acids, in particular hydrochloric acid or hydrobromic acid. A mixture of zinc chloride and gaseous hydrogen chloride is advantageously used as a conventional condensation catalyst system, wherein the water arising during the reaction is removed with the solvent by azeotropic distillation or as aqueous acid by distillation. Particularly good yields are achieved, according to EP 0 100 471 and DE 26 06 830 by adding an amine or quaternary ammonium salt as a third catalyst component. EP 0 850 937 A1 also describes the additional use of an amine, in particular tridecylamine (TDA×HCl), which, in its protonated state, may also assume the form of a quaternary ammonium salt.

Once the reaction is complete, the product must then be acetylated in order to obtain the storage-stable vitamin E acetate usual in commerce.

One disadvantage of this process, which is highly economic with regard to the yields achieved, is the issue of wastewater caused by the use and extractive separation of large quantities of zinc chloride. The catalyst components are conventionally extracted after the condensation with water or with a mixture of water and methanol. In this manner, it is possible to remove both the mixture of protonic acid/Lewis acid and the phase transfer catalyst from the crude tocopherol phase but, after such working up, the crude tocopherol phase may no longer be acylated at moderate temperatures, as the presence of a catalyst is required for mild, selective acylation with acetic anhydride.

In the stated patent literature, the acylation with acetic anhydride is either performed at elevated temperatures of >100° C., or, alternatively, a catalyst is added again. In this connection, both organic bases and Lewis or protonic acids have been described as catalysts for acylating the crude tocopherol. Once the reaction is complete, the catalyst and the acetic acid formed must be separated by extraction with water and a suitable organic extracting agent. The process accordingly comprises in total two complex extraction steps, if esterification is to be performed at moderate temperatures. If the subsequent acetylation is performed purely thermally in the presence of a catalyst by refluxing with acetic anhydride, a corresponding energy input is required.

It is not possible simply to recycle these aqueous zinc halide solutions arising after extraction because, in the case of condensation of TMHQ with isophytol, water, which deactivates the catalyst solution, is also formed during the reaction, in addition to the water required for extraction (c.f. Bull. Chem. Soc. Jpn., 68, (1995), pp. 3569 et seq. and Bull. Chem. Soc. Jpn., 69, (1996), p. 137, left hand column). Attempts to recycle the zinc halide phase extracted with water (approx. 20–60 wt. % $ZnCl_2$) and to reuse it for condensation, result in a reduction in reaction yield and poorer product quality. Evaporating this aqueous catalyst solution to regenerate pulverulent zinc halide involves complex solids handling and is not economic.

In EP 0 850 937 A1, Baldenius et al., the reaction is performed in a solvent which is immiscible or only slightly miscible with water, the catalyst phase is extracted with water after the reaction and, once the aqueous phase has been concentrated to approx. 60%–90%, the resultant catalyst solution is returned to the reaction at 20° C.-200° C. The disadvantage of this process is the fact that the zinc halide mixture assumes mash form at room temperature and may thus only be conveyed by special pumps designed for this purpose. In order to obtain the catalyst in liquid form, the mash must be heated to an appropriate temperature, which also entails considerable costs.

It is moreover necessary in this process to introduce the protonic acid, preferably hydrochloric acid, as a pure substance in gaseous form during the reaction. The water entering the reaction system due to the recycling of the catalyst mash and the water arising during the reaction are continuously removed during the reaction by azeotropic distillation. It should be noted that, once 1.5 mol of $H_2O$/mol of $ZnCl_2$ have been introduced, azeotropic removal of water may not occur. Larger quantities of water, however, deactivate the catalyst completely.

Another considerable disadvantage is the fact that the acylation catalyst is also removed from the organic phase during aqueous extraction of the catalyst solution. When this process is used, there is no option but either to add fresh catalyst in an additional step or alternatively to perform acylation thermally, which is costly in terms of energy. This disadvantage gave rise to the object to be achieved by the invention of providing a catalyst/solvent matrix which permits both the condensation and the post-acetylation to be performed at moderate temperatures without the necessity of costly addition of fresh catalyst after the condensation.

The selection of the solvent is of particular significance because the condensation solvent also predetermines the subsequent working up and ultimately the catalyst recycling medium.

Using solvents containing esters gives rise to a further difficulty, due to the presence of water during the reaction, in particular if it is economically essential to recycle the catalyst in the form of an aqueous solution. The concentration of water and the temperature required for condensation and ultimately the selection of the ester determine the rate of saponification. Esters of short chain alcohols, in particular, exhibit a strong tendency to saponify and are thus not suitable, readily recyclable solvents for the condensation reaction. In this manner, the ester used as a solvent gives rise to the organic acids and alcohols, which must be removed from the product in an elaborate separation process or which accumulate when the solvent is returned in the recirculation process.

With the exception of the stated literature, the described processes make no mention of the working up of the catalyst solutions used in the reaction.

SUMMARY OF THE INVENTION

The object of the invention is to provide an improved process for the production of α-DL-tocopherol esters and to regenerate the catalyst phase obtained in the reaction after working up in such a manner that it may straightforwardly be returned to the reaction without any reduction in catalytic activity. In particular, the object of the invention is to provide a process which permits the active catalyst solution to be recycled in an easily handleable, readily apportionable liquid form, reuse of the catalyst solution without resulting in any reduction in yield or impairment of product quality.

A further object of the invention is to provide a process which permits both the condensation and the reaction with acetic anhydride required for esterification of vitamin E formed "in situ" to yield vitamin E acetate to be performed at moderate temperature, without requiring repeated apportioning of the catalyst before the condensation and before the post-acetylation and simultaneously avoiding thermal post-acetylation.

In the present invention, moderate temperatures should be understood as temperatures below 100° C.

Another object of the invention is, in particular, to provide a process in which both, the reaction and the acetylation with acetic anhydride proceed at moderate temperature, in which both the reaction and the subsequent acetylation proceed using the same catalyst system and in which the catalyst may be recycled in the form of an acetic solution containing water, which is readily handleable and pumpable as a liquid at room temperature, (approximately 25° C.) without there being any loss in catalytic activity on repeated recycling.

The problems described above are solved by using a catalyst system comprising an aqueous hydrohalic acid, a zinc halide and optionally an elemental metal, in particular zinc, with acetic acid being used as solvent. Performing the highly selective reaction in acetic acid makes it possible, once the condensation has been performed, to separate the water of reaction together with the majority of the condensation catalyst as an acetic phase from the organic phase containing the product by simple phase separation. The active catalyst components remain in the organic phase in a sufficient concentration for the subsequent acetylation with an acylating agent, in particular acetic anhydride, to be performed efficiently and selectively at moderate temperatures. This allows the same catalyst system to be used without additional apportioning of a catalyst both for condensation and for acylation and simultaneously permits the acylation to be performed at moderate temperatures of between 0° C. and 60° C. Efficient separation of water in the acetic catalyst phase (catalyst phase I and II) means that the quantity of acetic anhydride required to produce the vitamin E acetate may be reduced, as the acylating agent is consumed stoichiometrically in the presence of water.

In this connection, using an organic carboxylic acid, in particular acetic acid, as solvent allows vitamin E acetate yields of >96%, before distillation to be achieved, wherein after the reaction, without the presence of the acylating agent, not inconsiderable quantities of vitamin E acetate are already present, in addition to the main product vitamin E. The presence of the main product may be explained by "in situ" esterification between vitamin E and acetic acid with formation of water which occurs in the presence of the condensation catalyst.

Using acetic acid as the preferred solvent and extracting agent for the catalyst solution after condensation allows the catalyst solution to be recycled in the form of a readily handleable, aqueous acetic solution, which may be regenerated by simple distillation of acetic acid and water in such a manner that none of the catalytically active components are lost with the distillate. The resultant catalyst solution may be returned to the reaction without loss of activity. Due to the phase separation of the tocopherol phase performed after condensation, which gives rise to the aqueous, acetic catalyst phase, it is possible, without adding further extracting agents and water, to obtain a crude tocopherol phase which exhibits a sufficient concentration of the catalyst components to ensure acylation at moderate temperatures, in particular between 20° C. and 40° C. Handling and the complexity of the plant for apportioning and pumping the catalyst solution are furthermore substantially simplified.

The majority of the catalyst may be separated after the condensation reaction from the vitamin E/vitamin E acetate phase by simple phase separation of the acetic phase (catalyst phase I), wherein an adequate catalyst concentration still remains in the organic phase in order to permit gentle, highly selective post-acetylation at moderate temperatures. After the acetylation, catalyst residues are removed from the vitamin E acetate phase by aqueous extraction and the resultant aqueous catalyst phase (catalyst phase II) is combined with the catalyst phase I obtained after condensation. These catalyst phases are most simply worked up by separation by distillation of a mixture of acetic acid and water without the active catalyst components being entrained in the distillate. An acetic, aqueous concentrated catalyst solution (recycled catalyst solution III) remains, which may be reused for the condensation.

This catalyst solution is also liquid at room temperature and, at moderate temperatures, constitutes a readily handleable and apportionable formulation of the active catalyst.

The invention relates to a process for the production of α-tocopherol acetate by condensation of TMHQ and a phytol derivative, in particular isophytol (IP), at moderate temperatures in the presence of a catalyst system including a zinc halide and a protonic acid and optionally an elemental metal, in particular zinc, in acetic acid as solvent. After the condensation reaction, the mixture of tocopherol/tocopherol acetate obtained after condensation is post-acetylated at moderate temperatures, in the presence of the condensation catalyst, which remains in the organic phase in sufficient concentration after separation of the acetic catalyst phase after condensation, with an aqueous, acetic catalyst solution being regenerated and recirculated. The zinc halide catalyst used preferably is selected from chlorides and bromides, as well as mixtures of these components. The basic chlorides and bromides of zinc, i.e. the corresponding oxy- and hydroxyhalides, also constitute active catalysts for the process according to the invention.

The condensation of the aromatic structural unit TMHQ with IP in the presence of a catalyst system comprising $ZnX_2$ and HY (X=halide, hydroxide, oxide; Y=anion of a Brønsted acid), and, optionally, an elemental metal, in particular zinc, added as a third catalyst component proceeds at good yields if the reaction is generally performed in a protic solvent extractable or miscible with water, preferably acetic acid, and the catalyst solution used for the condensation and subsequent acetylation is introduced into the reaction in the form of an aqueous, acetic solution of $ZnX_2$ and HY. The catalyst solution typically contains a zinc halide content of approx. 50 wt %–90 wt. %, 1 wt. %–10 wt. % of HY, 1 wt. %–30 wt. % of water and 1 wt. %–30 wt. % of acetic acid. The molar ratio between the active zinc halide component and water is approx. 1:4, the molar ratio of zinc halide to acetic acid being between 1:10 and 10:1.

The reaction of the components used as educt proceeds in excellent yields in acetic acid. In comparison with the esters conventionally used as solvent for the condensation, acetic acid has the advantages that a) it is inert under the reaction conditions, whereas corresponding conventional esters have a tendency to hydrolyze in the presence of the acid catalysts and water; b) that a mixture of vitamin E and vitamin E acetate is already contained at the condensation stage, such that the quantity of acylating agent may be reduced in the subsequent post-acetylation, c) that aqueous acetic acid is suitable for extracting the acid catalyst and for removing the water of condensation with the catalyst phase I; and d) that acetic acid may simultaneously be used as a solvent for the reaction and as a solvent medium for the active catalyst system. Even when the regenerated catalyst phase is continuously recycled with sub-stoichiometric replenishment of component HY, no loss of catalytic activity is observed, which is in turn manifested as constantly high selectivities and yields.

When the process is performed discontinuously, the acetic acid used as solvent may be added fresh for each batch. In a preferred embodiment, the acetic acid, obtained in a first batch as a secondary product upon acetylation with acetic anhydride, is used as the solvent. The acetic acid concentration relative to the introduced TMHQ may amount to approximately 10 wt. %–300 wt. %, wherein the best results are conventionally achieved at 50 wt. % to 150 wt. % of acetic acid relative to TMHQ.

The quantity of water may be varied within wide ranges and, in order to achieve good results, is generally adjusted to a concentration in the reaction mixture of $10^{-2-400}$ mol % relative to TMHQ, wherein a molar ratio of TMHQ:water of between 4 and 0.5 (400 mol % to 25 mol %) is preferably established. The quantity of water may be obtained by adding together the concentration of water which is introduced into the reaction in recycled catalyst solution III and the freshly replenished aqueous HY (catalyst/protonic acid). The concentration of water in the reaction mixture is substantially determined by the water content of the recycled catalyst phase III.

The condensation reaction is performed in the presence of the catalyst components $ZnX_2$/HY and, optionally an elemental metal, in acetic acid as solvent at temperatures of between 0° C. and 150° C., wherein the best results are achieved within a temperature range of from 40° C.–120° C. The subsequent acetylation is performed in the presence of the catalyst components $ZnX_2$/HY and optionally an elemental metal at temperatures of between 0° C. and 100° C., wherein the best results are achieved betweem 0° C. and 40° C.

According to the known patent literature, suitable Lewis acids are zinc salts, in particular halides such as zinc chloride and zinc bromide, wherein this terminology also includes the corresponding hydroxides arising under reaction conditions. The quantities of Lewis acids used relative to the introduced TMHQ are 10 mol %–200 mol %, in particular 20 mol %–50 mol %. When recycling the regenerated catalyst solutions, the Lewis acid concentration is substantially established by the Lewis acid content of the aqueous, acetic recycle solution.

The Lewis acid does not need to be introduced into the reaction as a purchased component, but may instead be produced "in situ" by mixing appropriate quantities of hydrohalic acid with the corresponding metal, in particular zinc. Once the catalyst solution has been regenerated, virtually all the corresponding zinc halide may be detected again, any missing quantities being made up by replenishment of the elemental metal and an aqueous hydrohalic acid up to the desired concentration.

According to the patent literature, protonic acids which may be used are mineral acids, in particular hydrohalic acids in concentrated form or in the form of the aqueous solutions thereof. Good results are in particular achieved when hydrogen chloride and hydrogen bromide are used, in particular, in the form of concentrated aqueous solutions thereof. Sulfuric acids, sulfuric acid/$SO_3$ mixtures with various $SO_3$ concentrations and superacids with an $H_0$ value of less than or equal to −11.9, such as for example perfluoroalkanoic acids, or mixtures of boric acid and oxalic acid may also be used as acids. The quantities of protonic acids used relative to the introduced TMHQ are 0.01 mol %–100 mol %, in particular 5 mol %–50 mol %. It is preferred to use concentrated solutions of hydrochloric acid and hydrogen bromide.

When recycling the regenerated catalyst solutions, the protonic acid concentration is substantially established by the protonic acid content of the aqueous, acetic recycle solution.

The sequence of addition of educt and catalyst is, in principle, immaterial (this does not apply to isophytol, which is added finally to the mixture of the other components) and is understood by way of example in the following description.

DETAILED DESCRIPTION OF THE PREFERRED EMBODIMENTS

Figure 1:
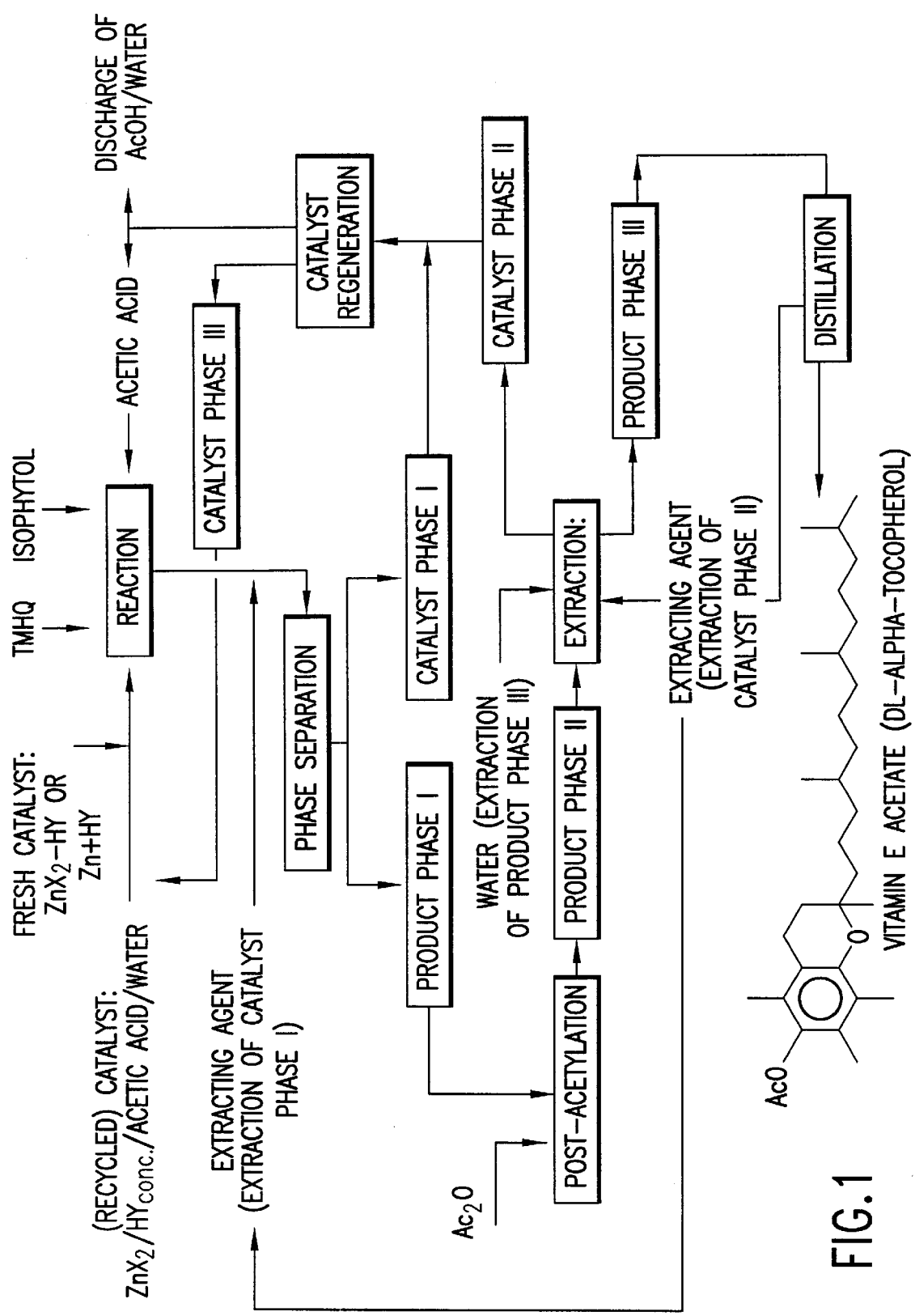
FIG. 1 is a flow chart showing the process of the invention.

The process of the invention may, for example, be illustrated by the simplified flow chart shown in the FIGURE.

In a preferred embodiment, when the process is started, the acetic acid used as solvent (for example, from the preceding batch of vitamin E acetate production after acylation with acetic anhydride or as fresh solvent) is initially introduced and the catalyst components, the aqueous hydrohalic acid and the appropriate zinc halide and, optionally, elemental zinc, are dissolved therein. The aromatic structural unit TMHQ is added to this solution. The resultant suspension is adjusted to the reaction temperature. IP, optionally as an acetic acid solution, is apportioned to this mixture over a period of 2–4 hours. Once the reaction is complete, the reaction mixture is cooled to room temperature, when two defined phases are formed, the catalyst phase (catalyst phase I) and the product phase (product phase I).

The lower, heavy phase (catalyst phase I) contains vitamin E/vitamin E acetate as a secondary product and mainly contains an aqueous, acetic solution of the catalyst components. The proportion of product components (vitamin E and vitamin E acetate) in the catalyst phase I is approx. 0.1 mol %–5 mol %, usually 0.5mol %–2 mol % of the total quantity of product formed. The product fractions present in the catalyst phase may be recovered by simple extraction with a suitable solvent and are then combined with the upper product phase. When the process is performed discontinuously, it is also possible to simply add a non-polar solvent having elevated solvency for vitamin E and vitamin E acetate, in particular, an alkane, an aromatic solvent or a corresponding ester. By simply stirring with such solvents, the vitamin E/vitamin E acetate content in the catalyst phase I may be reduced to such an extent that only traces remain, thus, causing no appreciable loss of yield.

The upper phase (product phase I) contains residues of the catalyst components $ZnX_2$ and HY and, together with the extracting agent, a mixture of vitamin E and vitamin E acetate as the main constituents. Depending upon the manner in which the reaction is performed, the ratio between vitamin E and vitamin E acetate is in the range between 10:1 and 1:1, with the ratio obtained after condensation usually being between 5:1 and 2:1. The primary determining parameters for the ratio between vitamin E and vitamin E acetate may be identified as the concentration of water in the reaction solution and the reaction temperature, in particular the manner in which the reaction is performed, as the proportion of vitamin E acetate is increased when water is removed azeotropically from the system.

The quantity of catalyst remaining in the upper product phase is sufficient for acetylating the unesterified quantity of vitamin E present together with the vitamin E acetate at moderate temperatures.

After phase separation of catalyst phase I from product phase I, the fraction of product components, which constitute approx. 0.1 mol %–5 mol % of the total quantity of product formed, are removed from the catalyst phase by extraction. Extracting agents which may be used in the present invention are any suitable solvents which are immiscible or only slightly miscible with the catalyst phase, in particular aliphatic, cycloaliphatic or aromatic solvents. Pentane, hexane, heptane, octane, nonane, decalin, ligroin, petroleum ether, cyclohexane, benzene, toluene, xylene, or halogenated derivatives of the solvent are examples of suitable solvents. Other usual solvents such as esters, in particular carbonate esters and aliphatic carboxylic acid esters, and aliphatic alcohols, together with mixtures of the stated groups of solvents, are also suitable for this extraction.

The extraction proceeds very efficiently even with small quantities of aliphatic extracting agent. The quantity of extracting agent may be varied within ranges between 10 wt. % and 200 wt. %, relative to the catalyst phase I to be extracted.

The extraction phase, which substantially comprises vitamin E/vitamin E acetate and the extracting agent, is combined with the product phase I, so producing a combined phase, product phase II, additively composed of product phase I, which contains the majority of the vitamin E and vitamin E acetate formed. This phase contains 95%–99.1% of the total quantity of vitamin E+vitamin E acetate formed after the condensation reaction, and the extract from catalyst phase I, which contains 0.1%–5% of the total quantity of vitamin E and vitamin E acetate formed.

As already stated, the product content in catalyst phase I may also be reduced to <0.1 wt. % without extraction by simply adding an appropriate quantity of a water-insoluble solvent which is immiscible with the catalyst phase. Product phase I, which contains a mixture of vitamin E and vitamin E acetate is then reacted at moderate temperatures by reaction with an acylating agent.

In this manner, it is possible to remove virtually all the water from the product phase I obtained after phase separation, which water would disrupt the subsequent acylation by causing additional consumption of acetic anhydride.

Acylation is then performed in a simple manner in the water-insoluble, hydrophobic solvent, without the selectivity or rate of the reaction being substantially affected. The volume ratio between the water-insoluble solvent and product phase I may be varied within wide ranges, the ratio generally being 0.5 to 5, depending upon the nature of the solvent used. Good results are achieved, for example, by using aliphatic hydrocarbons, such as hexane or heptane, or using aromatic hydrocarbons, such as toluene, for the solvent.

Post-acetylation may be performed batch-wise or continuously, wherein product phase I is composed of acetic acid, the extracting agent, vitamin E and vitamin E acetate. The residual water concentration present in the phase to be acylated is optionally eliminated by adding an appropriate excess of acetic anhydride, wherein acetic acid is formed, which is, in any event, present in the reaction system from the outset.

In an advantageous embodiment, product phase I is combined with acetic anhydride, wherein the reaction is effectively catalyzed even at room temperature, by the presence of the protonic acid/Lewis acid catalyst system. Depending upon the manner in which the reaction is performed and the concentration of the catalyst component, the reaction may proceed within a temperature range between −20° C. and 100° C., preferably between 0° C. and 60° C., particularly preferably at room temperature.

Once the reaction is complete, product phase II is obtained, which now contains vitamin E in a concentration of only <1%, relative to vitamin E acetate. This product phase is worked up in a subsequent step by catalyst extraction with water and, optionally, a cosolvent, preferably methanol or ethanol, wherein a solvent which is immiscible or only slightly miscible with water may simultaneously be used to promote phase separation, in order to remove any product residues from the aqueous, acetic catalyst phase II so obtained. If the water-insoluble solvent has already been added before the first phase separation (production of catalyst and product phase I), no additional solvent needs to be added at this point and the catalyst residues are simply extracted with water or a water/cosolvent mixture.

The quantity of the aqueous extracting medium, in the simplest case water, may be varied within wide ranges and is in particular dependent upon the nature of the Lewis acid used and the desired degree of extraction. Good results are achieved, if the product phase is washed twice or three times with 1 to 10 vol. % of water. The manner in which this extraction is performed is relatively non-critical and it may be performed continuously as counter-current extraction. In the simplest case, product phase II is extracted by stirring in succession with appropriate quantities of water or aqueous alcohol solution.

The same criteria apply to the selection of the extracting agent for the aqueous catalyst phase II as have already been indicated above for the extraction of catalyst phase I. It is preferred to perform the extraction of catalyst phase I and the extraction of catalyst phase II in the same extracting agent. It is particularly advantageous to perform this separation of product (vitamin E acetate) and catalyst ($ZnX_2$/HY) as an optionally multistage counter-current extraction.

After extraction of product phase II with water and optionally a cosolvent such as methanol or ethanol, an aqueous, acetic phase containing the catalyst components, catalyst phase II, is obtained. This catalyst phase II, which contains the acylation catalysts, is combined with catalyst phase I obtained after condensation. An aqueous, acetic catalyst phase is obtained, which contains the entire quantity of the active catalyst components $ZnX_2$ and a large proportion of the active catalyst component HY.

This catalyst phase is treated by appropriate processing in such a manner that a phase containing the catalyst components, catalyst phase III, is obtained which, once the partially consumed component HY has been replenished, may be reused for condensation of the building blocks TMHQ and IP. Catalyst regeneration substantially comprises partial removal of acetic acid and/or water, in which the catalyst components $ZnX_2$ and HY substantially remain in a concentrated water/acetic acid solution. In the simplest case, the combined catalyst phases I and II are distilled off for this purpose, wherein water and acetic acid are obtained as the distillate, without HY being entrained in the distillate in the form of a concentrated, aqueous solution.

Distillation and the associated regeneration of the catalyst phase are performed at a pressure of 0.1 Torr to 760 Torr. Regeneration of the combined catalyst phases I and II by distillation is performed as a function of the established pressure within a temperature range of from 20° C.–200° C. The possibility of catalyst regeneration at reduced pressure and corresponding moderate temperatures, offers additional advantages with regard to the selection of the materials for the apparatus used. In another embodiment according to the invention, the catalyst regeneration is performed by evaporating the combined catalyst phases I and II such that some HY is also removed by distillation together with the water and acetic acid. The resultant catalyst phase III must then be made up with an appropriate concentration of HY in order to maintain complete catalytic activity.

Apart from by the described distillation methods, the combined catalyst phase may also be regenerated by alternative methods, in particular by separating water and/or acetic by separation using a suitable membrane. According to this alternative, the active catalyst solution is concentrated by selective removal of acetic acid and/or water, again leaving a catalyst solution III which, as stated above, contains the active catalyst components together with the acetic acid/water concentration.

Even after repeated recycling, the catalyst solutions III obtained using the described methods are of a sufficiently low viscosity within a temperature range of from 0° C.–200° C. to be conveyed in the liquid state with suitable pumps, without the catalyst components crystallizing, which entails additional recycling measures. The increase in viscosity of the regenerated catalyst solution, which is observed as the number of cyclic components rises, may straightforwardly be remedied by adding at least a proportion of the condensation solvent, acetic acid, to the regenerated catalyst phase. The acetic acid, used in this case as diluent and solvent, may also be added directly during regeneration of the combined catalyst phases I and II during distillation. In this method, it is substantially an acetic, virtually anhydrous solution of the catalyst system which is recycled.

The condensation according to the invention of TMHQ with IP in acetic acid as solvent and the described method for regenerating the catalyst solution as an aqueous catalyst solution containing acetic acid and $ZnX_2$/HY constitute a straightforward, efficient process for the production of vitamin E acetate which permits a constant catalytic activity of the catalyst used with little or no replenishment of catalyst component HY.

By producing vitamin E acetate starting from TMHQ and IP according to the invention, it has proved possible to find a solvent/catalyst matrix which, by using a water-soluble, water-extractable solvent, in particular acetic acid, makes it possible to achieve selective product formation after condensation and also to achieve separation of the condensation catalyst from the resultant product phase that contains vitamin E/vitamin E acetate and acetic acid.

Once the catalyst has been separated from the vitamin E/vitamin E acetate phase, an adequate catalyst concentration is provided for subsequent acylation with a suitable acylating agent at moderate temperatures, while the content of water, which disrupts acylation, is simultaneously reduced. After acylation with a suitable acylating agent to obtain the product, vitamin E acetate, the catalyst phase is extracted with a suitable aqueous extracting agent and, by regenerating the resultant catalyst phase with removal of water/acetic acid, an active catalyst phase III, which is readily handleable at moderate temperatures, is obtained, which may repeatedly be used as the catalyst solution without loss of activity.

The following Examples illustrate the process according to the invention. The content of the mixtures obtained after condensation and the content of the products were quantified by comparative analysis of the products relative to commercially available preparations (Fluka: 98.5% vitamin E acetate).

TMHQ=trimethylhydroquinone
IP=isophytol
TMHQ-DA=trimethylhydroquinone diester

EXAMPLES 1–4

112.6 g of $ZnBr_2$, 300 ml (315 g) of glacial acetic acid and 12.64 g of concentrated hydrobromic acid (48 wt. %) are initially introduced into a 2 liter, four-necked flask and 194.1 g of TMHQ (1.276 mol) are then stirred in. After briefly flushing the system with nitrogen at room temperature, the temperature is raised to 80° C. within 10 minutes. 395 g of IP (1.31 mol) are then added within 2 hours at 80° C. and stirring is then continued for 1 hour at 80° C.

After cooling to room temperature, 900 ml of n-hexane are added and product phase I is separated from catalyst phase I. An at least stoichiometric quantity of acetic anhydride is then added to product phase I within 30 minutes in such a manner that the reaction temperature does not exceed 25° C. and the reaction is then allowed to continue for a further 15 minutes.

350 ml of n-hexane and 250 ml of water are then added to the reaction solution and the mixture stirred vigorously for approximately 10 minutes. The emulsion is separated in a separating funnel and the organic phase washed twice with 50 ml of water.

The resultant product phase III is evaporated to constant weight in a rotary evaporator at 60° C. and 1 mbar. The recovered n-hexane may be reused for subsequent extractions. Once the solvent has been removed in a rotary evaporator, 615.7 g of a yellow oil are obtained having a product content of 95.2% vitamin E acetate, according to quantitative HPLC analysis. The yield relative to TMHQ is accordingly 97.2%.

The two acetic extracts containing water (catalyst phase I) are combined with catalyst phase II and evaporated to a bottom temperature of 146° C. by simple distillation consisting of a Liebig condenser with a Claisen stillhead.

154.4 g of residue (violet solution) is thus obtained which is distinguished by being readily pumpable and handleable at room temperature. No solidification of the solution is observed even after extended storage at room temperature. The composition of the bottom product is as follows:

| | |
|---|---|
| 71.3% | $ZnBr_2$ |
| 3.6% | HBr |
| 17.9% | water |
| 5% | AcOH |

The distillate from catalyst recycling contains no HBr. After replenishment of the lacking concentration of active catalyst components, this catalyst solution is recycled three times, wherein no reduction in catalyst activity is observed. The following yields of vitamin E acetate relative to TMHQ are obtained in succession:

| | | |
|---|---|---|
| Example 2 | 1st recycling | 97.0% |
| Example 3 | 2nd recycling | 96.8% |
| Example 4 | 3rd recycling | 97.5% |

EXAMPLES 5–8

Example 1 is reproduced (=Example 5) and the resultant residue is provided with the quantities of $ZnBr_2$, HBr and acetic acid stated in Table I. 10 Wt. % of the catalyst solution obtained in each case is removed for a complete quantification of composition for analytical purposes and replaced by fresh catalyst components.

TABLE 1

| Test Example | TMHQ [g] mMol | Isophytol [g] mMol | Mol-% | Zinc bromide recycled [g] mMol | Zinc bromide fresh [g] mMol | Zinc bromide total [g] mMol | HBr 48% recycled [g] mMol | HBr 48% fresh [g] mMol | HBr 48% total [g] mMol |
|---|---|---|---|---|---|---|---|---|---|
| 5 | 194.1 | 395.1 | 105 | — | 112.6 | 112.6 | — | 12.64 | 6.07 |
|   | 1250 | 1313 |     | — | 500   | 500   | — | 75    | 75   |
| 6 | 194.1 | 395.1 | 105 | 104.0 | 8.6  | 112.6 | 5.1  | 1.9  | 6.1 |
|   | 1250 | 1313 |     | 461.8 | 38.2 | 500   | 63.6 | 11.4 | 75  |
| 7 | 194.1 | 395.1 | 105 | 105.8 | 6.8  | 112.6 | 5.2  | 1.74 | 6.1 |
|   | 1250 | 1313 |     | 469.8 | 30.2 | 500   | 64.7 | 10.3 | 75  |
| 8 | 194.1 | 395.1 | 105 | 107.3 | 5.3  | 112.6 | 5.5  | 1.2  | 18.2 |
|   | 1250 | 1313 |     | 476.6 | 23.4 | 500   | 67.7 | 7.3  | 225  |

| Test Example | H$_2$O recycled [g] mMol | H$_2$O total [g] mMol | Ac$_2$O NaAc [g] mMol | Tocopherol-Phase [g] weight | Tocopherol-Phase (HPLC) % E % EAc | Tocopherol-Phase mm E mmEAc | Yield % of theoretical TMHQ-DA |
|---|---|---|---|---|---|---|---|
| 5 | — | 6.6    | 175.5  | 1332.5 | 35.3 | 1092.1 | 97.4 |
|   | — | 364.9  | 1651.0 |        | 7.2  | 203.0  |      |
| 6 | 26.1   | 6.6   | 198.2  | 1340   | 33.4 | 1039.1 | 96.9 |
|   | 1440.3 | 366.3 | 1941.0 |        | 7.7  | 218.3  |      |
| 7 | 25.3   | 6.6   | 199.9  | 1336.4 | 34.5 | 1070.5 | 97.1 |
|   | 1403.5 | 366.3 | 1958.3 |        | 7.6  | 214.6  |      |
| 8 | 25.7   | 19.73 | 222.3  | 1332.1 | 37.2 | 1150.5 | 99.1 |
|   | 1426.6 | 1095  | 2333.8 |        | 5.3  | 149.4  |      |

EXAMPLES 9–10

The following Examples, set forth in Table 2, demonstrate that, instead of zinc bromide, a mixture of aqueous HBr and elemental zinc may also be used as a catalyst system which provides "in situ" the concentration of zinc bromide required for selective catalysis. When recycling the catalyst solution, any losses of zinc bromide occurring as a result of the selected discharge rate are remedied by addition of zinc and HBr at the beginning of the new cycle. In Example 9, zinc bromide is initially used as in Example 1. When the catalyst solution from Example 9 is recycled, replenishment is made only by means of Zn and HBr.

In Example 10, 1.32 g of Zn (20 mmol; 1.6 mol % relative to TMHQ) are added. The catalyst components are replenished at the catalyst phase III step before distillation to adjust the water content.

TABLE 2

| Test Example | TMHQ [g] mMol | Isophytol [g] mMol | Mol-% | Zinc bromide recycled [g] mMol | Zinc bromide fresh [g] mMol | Zinc bromide total [g] mMol | HBr 48% recycled [g] mMol | HBr 48% fresh [g] mMol | HBr 48% total [g] mMol |
|---|---|---|---|---|---|---|---|---|---|
| 9 | 194.1 | 395.1 | 105 | — | 112.6 | 112.6 | — | 12.64 | 6.07 |
|   | 1250 | 1313 |     | — | 500   | 500   | — | 75    | 75   |
| 10 | 194.1 | 395.1 | 105 | 108.0 | / | 112.6 | 5.2  | 8.43 | 18.2 |
|    | 1250 | 1313 |     | 479.5 |   | 500   | 64.7 | 50   | 115  |

| Test Example | H$_2$O recycled [g] mMol | H$_2$O total [g] mMol | Ac$_2$O [g] mMol | Tocopherol-Phase [g] weight | Tocopherol-Phase (HPLC) % E % EAc | Tocopherol-Phase mm E mmEAc | Yield % of theoretical TMHQ-DA |
|---|---|---|---|---|---|---|---|
| 9 | — | 6.6    | 175.5  | 1325 | 34.9 | 1070  | 96.7 |
|   | — | 364.9  | 1651.0 |      | 7.2  | 203.0 |      |
| 10 | 13.63  | 19.73 | 222.3  | 1332 | 37.2 | 1150.5 | 99.1 |
|    | 1426.6 | 1095  | 2333.8 |      | 5.3  | 149.4  |      |

What is claimed is:

1. A process for the production of α-tocopherol acetate in a recirculating process comprising:

condensing trimethylhydroquinone and isophytol in the presence of a catalyst system comprising a zinc halide and an aqueous protonic acid and, optionally, an elemental metal, in a polar solvent/water mixture that is extractable or miscible with water, wherein:

i) α-tocopherol initially obtained in the condensation reaction is separated from an aqueous catalyst phase and esterfied with an accylating agent, ii) a solution of the catalysts obtained after working up by aqueous extraction is regenerated and the solution containing acetic acid is returned to the reaction, and iii) the mixture of catalysts comprising zinchalide and protonic acid is concentrated and reintroduced into the reaction in liquid form.

2. The process according to claim 1, wherein the zinc halide is selected from the group consisting of chloride, bromide, oxychloride, hydroxychloride, oxybromide, hydroxybromide and mixtures thereof.

3. The process according to claim 1, wherein the protonic acid comprises hydrochloric acid or hydrobromic acid.

4. The process according to claim 1, wherein the elemental metal comprises zinc.

5. The process according to claim 1, wherein the solvent for the mixture of catalysts comprises acetic acid.

6. The process according to claim 1, wherein an extracting agent for the mixture of catalysts comprises acetic acid.

7. The process according to claim 1, wherein the acylating agent comprises acetic anhydride.

8. The process according to claim 1, wherein the aqueous, acetic catalyst mixture is concentrated by distillation or membrane separation.

9. The process according to claim 1, comprising carrying out the reaction continuously repeatedly with recirculation.

* * * * *